United States Patent [19]

Rusz

[11] Patent Number: 4,581,945
[45] Date of Patent: Apr. 15, 1986

[54] PRESSURE TO VOLTAGE CONVERTER FOR MEASURING GAS GLOW RATES

[76] Inventor: Tibor Rusz, 761 West St., Pittsfield, Mass. 01201

[21] Appl. No.: 685,796

[22] Filed: Dec. 24, 1984

[51] Int. Cl.[4] .............................................. G01F 1/50
[52] U.S. Cl. ...................................... 73/861.52; 73/3; 73/198; 73/861.02; 128/205.23
[58] Field of Search ................ 73/198, 861.02, 861.42, 73/861.47, 861.48, 861.52, 3; 128/205.23

[56] References Cited

U.S. PATENT DOCUMENTS

| | | | |
|---|---|---|---|
| 1,778,716 | 10/1930 | Foregger | 73/198 X |
| 2,099,842 | 11/1937 | Connell | 128/205.23 X |
| 3,071,160 | 1/1963 | Weichbrod | 73/861.52 X |
| 3,713,337 | 1/1973 | Stroman | 73/861.42 |

Primary Examiner—Charles A. Ruehl
Attorney, Agent, or Firm—Arthur K. Hooks

[57] ABSTRACT

A converter has a pressure to voltage transducer connected to an amplifier. A laminar gas flow element (L.F.E.) may be connected to the transducer and the converter output voltage is a measure of the gas flow rate through the L.F.E. The converter gain may be switched from one value when one kind of anesthetic gas is being monitored to another gain values when a second gas is used. The ratio of the one gain values to the second is made equal to the ratio of viscosities of the second gas to that of the first so that recalibration is not necessary when the kind of gas in use is changed. Further, the absolute values of the stepped gains with fixed ratio are adjusted vernierly to produce a predetermined output voltage for each L.F.E. with a known rate of gas flowing, which absolute gain value in each case may be recorded as a characterization of each particular L.F.E. After such characterizations are made, no further calibrations of L.F.E. or converters are needed and any L.F.E. combined with any converter, with the converter gain reset of the "characterizing gain" associated with the particular L.F.E., provides a calibrated anesthetic gas flow measuring instrument.

9 Claims, 2 Drawing Figures

PRESSURE TO VOLTAGE CONVERTER FOR MEASURING GAS GLOW RATES

BACKGROUND OF THE INVENTION

This invention relates to a pressure to voltage converter for use in a gas flow measuring instrument for monitoring the flow of gasses, for example anesthetic gasses administered by an anesthesiologist to a patient undergoing surgery entailing forced ventilation, and more particularly relates to such a converter that is capable of an accurate flow rate indication for any of several gasses that may be used and is capable of such accurate indication when used with any one of a variety of laminar flow sensing elements.

For a patient undergoing surgery the anesthesiologist not only administers an anesthetizing agent to render the patient unconscious but also usually administers a drug having the additional effect of inducing complete muscle paralysis to the extent that there is no involuntary movement of muscles that may interfere with the surgery. For this reason and others it is often necessary to provide a patient with forced pulmonary ventilation. It is especially important with forced ventilation that includes the administration of gasses such a nitrous oxide, oxygen or helium, that are intended to alter the state of the patient, that the flow rate of such body altering drugs be carefully monitored and controlled.

The measurement of the low gas flow rates of interest here, wherein the Reynolds number can conveniently be kept low, may employ a simple laminar flow sensing element (L.F.E.) comprised of a pipe, a bundle of capillaries built into the pipe and two ports, one near each pipe end. The differential pressure existing between the two ports is nearly linearly related to the rate of flow of a gas through the pipe. Thus a pressure to voltage converter connected to the two output pressure ports of the L.F.E. may provide an output voltage very nearly linearly related to the gas flow rate.

To accommodate different applications for several gasses and the lung capacities of small children to adults, the gas flow rates to be measured range from about 0.05 to 800 liters per minute (based upon the use of air). However, as many as six sizes of laminar flow elements are needed to cover this range. It has therefore been necessary to calibrate the combination of each of these L.F.E.'s with the particular pressure to voltage converter that will be used. Such a calibration procedure involves providing the gas of interest at a known flow rate to determine the correlation that will exist between flow rate and output voltage.

Furthermore, any two L.F.E.'s of the same size are likely to have somewhat different sensitivities and each must be calibrated individually in combination with the particular converter that will be used.

In addition, since the different gasses to be used (e.g., air, oxygen and nitrous oxide) have drastically different viscosities, the above mentioned calibrations must be effected for each gas to be used. Thus, for a particular medical procedure, it may be necessary for the anesthesiologist to assemble several combinations of an L.F.E. and a converter for use during the operation and calibrate each combination before they can be used.

It is therefore an object of this invention to provide a differential pressure to voltage converter with which any previously characterized laminar flow element can be readily combined to provide a calibrated output voltage.

It is another object of this invention to provide such a converter whose sensitivity can be simply switched to permit calibrated operation instantly when changing from the use of one gas to another.

It is yet another object of this invention to provide compensation for the small non-linearity that exists in the L.F.E.'s.

SUMMARY OF THE INVENTION

A pressure to voltage converter is provided for use in a specialized gas flow measuring apparatus for monitoring the flow of gasses especially as administered by an anesthesiologist to a patient undergoing surgery. The converter includes a differential pressure to voltage transducer that is adapted for attachment to two output pressure ports of a laminar flow sensing element. The converter also includes a voltage amplifier having an input connected to the output of the differential pressure to voltage transducer. The amplifier includes a gain-steps switching means for changing the gain of the amplifier in steps from a first gain value to a second gain value wherein the ratio of the second to the first gains is equal to the ratio to the viscosity of a gas of a first kind to that of a gas of a second kind.

Thus for instance when the anesthesiologist has been using the gas of the first kind and needs to change to the use of the gas of the second kind, he may switch the voltage converter of this invention very simply to the second gain value and continue accurate monitoring of the gas flow rates without recalibration of the converter or without the need for a second converter precalibrated for use with the second gas.

The converter of this invention may also include a vernier gain adjusting means for adjusting the combined transducer and amplifier gain so that a predetermined voltage at the output of the voltage amplifier is produced when gas of a known kind is flowing at a known rate through a particular laminar flow sensing element, and for reestablishing that gain in the future. That particular transducer plus amplifier gain is reestablished in practice whenever that particular laminar flow element is used with that same converter. Thus that characterizing gain or the equivalent thereof is advantageously recorded directly on the laminar flow element body. For all such laminar flow elements having been so characterized, any one of them may be used with any converter of this invention by reestablishing the characterizing gain via the converter's vernier adjusting gain means.

DESCRIPTION OF THE PREFERRED EMBODIMENT

Figure 1:
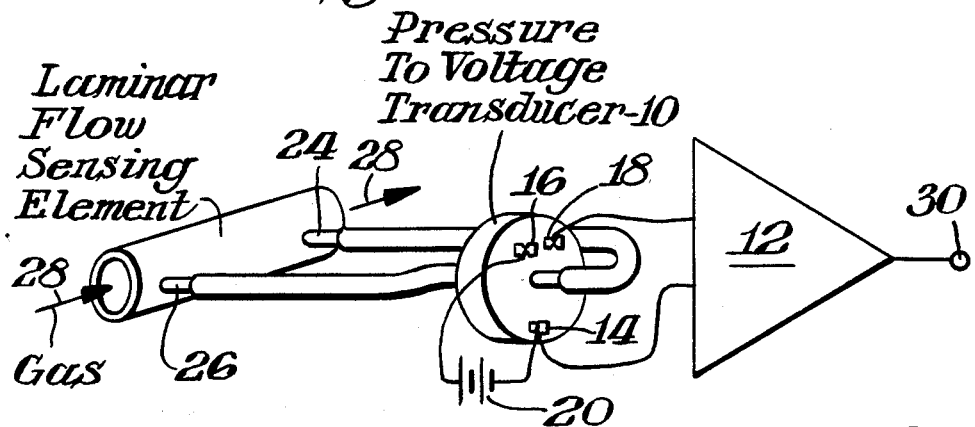
FIG. 1 shows a diagram of a laminar flow sensing element (L.F.E.) connected to the input of a pressure to voltage converter of the prior art.

A pressure to voltage converter is comprised of the two components, namely a transducer 10 of pressure to voltage and a voltage amplifier 12 as is illustrated in FIG. 1. The transducer 10 has three electrical terminals, i.e. a circuit ground point terminal 14, a power supply input terminal 16 and a voltage output terminal 18. The output voltage generated by the transducer 10 appears across terminals 14 and 18 which are connected to the input of the amplifier 12. The transducer is powered by a battery 20 that is connected to transducer terminals 14 and 16.

Also shown in FIG. 1 is a laminar flow sensing element 22 (L.F.E.) which has two output pressure ports 24 and 26. When a gas, represented in FIG. 1 by the arrows 28, flows through the L.F.E. 22, a pressure is developed across ports 24 and 26 that is directly related to the rate of flow of the gas 28. Thus the output voltage at the output 30 of amplifier 12 is a direct measure of the flow rate of the gas 28.

Figure 2:
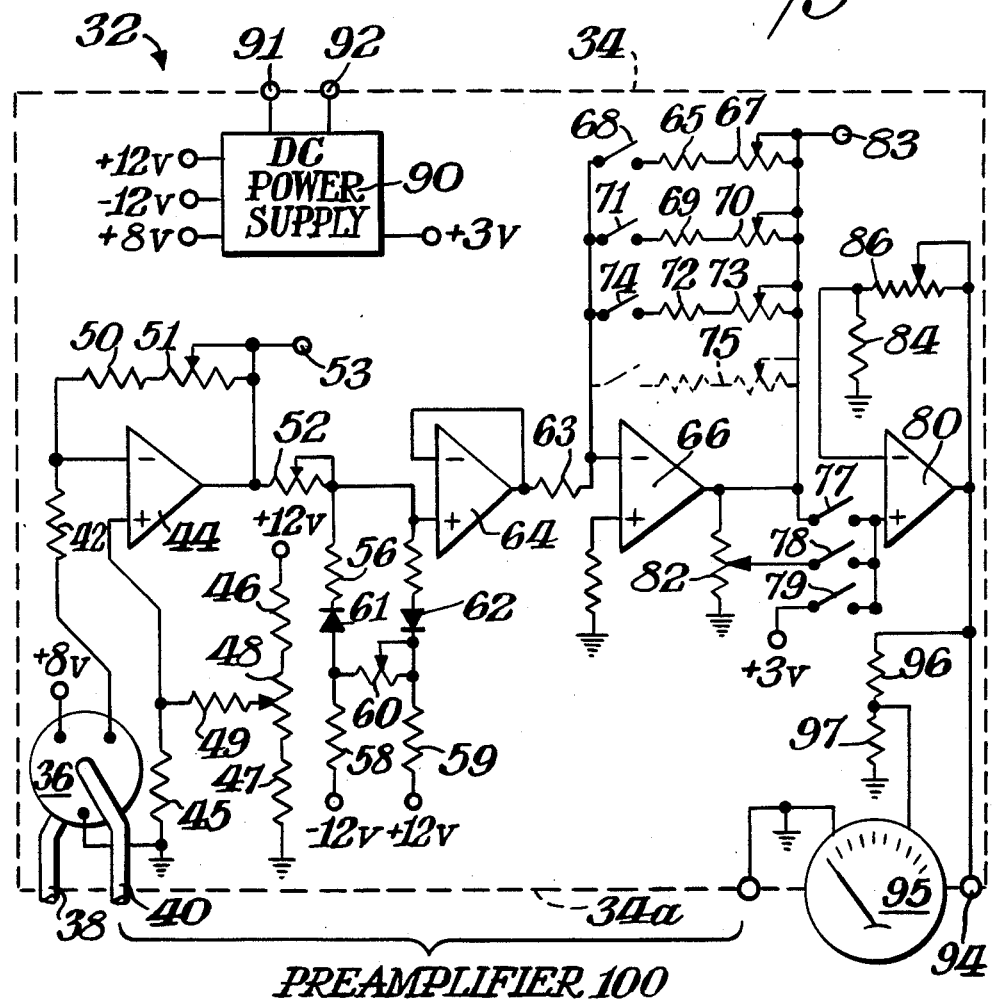
FIG. 2 shows a schematic and circuit diagram of the preferred embodiment of a pressure to voltage converter of this invention.

The preferred embodiment of the pressure to voltage converter 32 is illustrated in FIG. 2. A housing, represented by a broken line 34, has a front panel 34a. A silicon-diaphragm-type pressure-to-voltage transducer 36 has two input pressure ports 38 and 40 extending to the front panel 34a for access by the operator who will connect the output ports of an L.F.E. (not shown) thereto. Any other pressure-to-voltage transducer, such as a piezoelectric or a variable reluctance transducer type, may be used if it is essentially linear up to 10 cm $H_2$) of input pressure.

The voltage output from transducer 36 is connected through resistor 42 to the minus input of an operational amplifier 44. A high impedance "zero-setting" network is composed of a voltage divider circuit employing series resistors 46 and 47 and potentiometer 48. The variable arm of the potentiometer 48 is connected through resistor 49 to the plus input of operational amplifier 44. The function of this zero-setting network is described further below. Resistor 45 connects the plus input of amplifier 44 to ground.

The feedback network connected around operational amplifier 44 consists of a resistor 50 and a potentiometer 51. The output of operational amplifier 44 is connected to a network for compensating for the nonlinearity that is characteristic of laminar flow sensing elements (L.F.E.'s). Laminar flow sensing elements of all flow ratings were found to exhibit an output-differential-pressure function versus gas flow rate that deviates from a best straight line fit in essentially the same way and the same amount over the rated flow rate range. For example the peak deviations from best straight line fit of each L.F.E. alone was about ±2%. This linearizing network after potentiometers 52 and 60 are factory adjusted to give a best straight line fit produces a signal at the input of the following unit gain amplifier (64), which signal is an essentially linear function of the flow rate through any one of the L.F.E.'s that is connected to the converter, namely linear to within ±0.5% or less. The linearizing network consists of resistors 56, 57, 58 and 59 and potentiometers 52 and 60 as well as diodes 61 and 62 and is connected to a source of −12 volts and +12 volts as is seen in FIG. 2.

The output of the linearizing network is connected to the plus input of the unity gain operational amplifier 64. A resistor 63 connects the output of amplifier 64 to the minus input of amplifier 66. Amplifier 66 has three paralleled feedback circuits operable one at a time. One is a resistor 65 and potentiometer 67 connected in series with switch 68. Another is a resistor 69 and potentiometer 70 in series with a switch 71. A third is resistor 72 and potentiometer 73 in series with a switch 74. Others, indicated by the dashed line circuit 75, may be added to accomodate other gasses as needed.

Mechanically associated with the switches 68, 71 and 74 are three more switches 77, 78 and 79 and their mechanical linkage (not illustrated) is as follows:

Five of these switches 68, 71, 82, 78 and 79 are push button switches mounted on the front panel 34a of the converter 32, and are so mechanically linked that only one of these push buttons (not shown) can be pushed in at a given time. For example, if the push button of switch 68 is already in, it will pop out when any one of the other four is pushed in.

Pushing in any one button of these five switches closes at least the corresponding switch, e.g. pushing in the button of switch 68 will close switch 68.

Switch 77, having no associated push button, will close when the push button of anyone of switches 68, 71 or 74 is pushed in. For example, pushing in the push button of switch 68 closes switch 68 and switch 77.

Pushing in the button of switch 78 closes switch 78 and switch 74.

Pushing in the button of switch 79 only closes switch 79.

When switch 77 is closed, the output of amplifier 66 is connected to the plus input of amplifier 80. Or when switch 78 is pushed closed the output of amplifier 66 is tapped off of voltage dividing potentiometer 82 and connected to the input of amplifier 80. Or when switch 79 is pushed closed, 3 volts is applied to the plus input of amplifier 80. How these switches may be used is explained further below.

The amplifier 80 has a feedback network from the output to minus input including an input resistor 84 and a ten turn potentiometer 86 which allows very fine adjustment of the gain of amplifier 80.

A DC power supply 90 may be powered from the 110 V AC line via terminals 91 and 92 located in the rear wall of the housing 34. Power supply 90 provides several regulated DC voltages, i.e. +12 volts, −12 volts, +8 volts, and +3 volts, all with respect to ground.

The output of amplifier 80 is connected to the output terminal 94 on the front panel 34a. A volt meter 95 is also mounted on front panel 34a and is connected to the output of amplifier 80 via a voltage divider composed of resistors 96 and 97.

A laboratory model of the converter 32 shown in FIG. 2 has been built and tested. The silicon diaphragm transducer 36 is a model 163 PC 01D36 supplied by the Micro Switch Division of Honeywell Inc. It has a sensitivity of 0.5 V/centimeter of water pressure when powered from a DC source of exactly 8 volts. However, it produces an output voltage of 3.5 volts at zero pressure. Therefore, the potentiometer 48 will be adjusted at the factory to compensate and nullify at test point 3 for the zero-pressure output voltage of the transducer 36. The adjustment is made so that at zero-pressure between ports 38 and 40, a zero voltage is produced at the internal factory test points 55 and 83.

Factory adjustment of potentiometer 67 will be made under the conditions that a gas pressure is provided (any gas, e.g. air) corresponding to 8 centimeters of water between the transducer ports 38 and 40 and switch 68 is pushed closed so that exactly 5.520 volts appears at test point terminal 83. Factory adjustment of potentiometer 70 will be made under the conditions that air pressure is provided corresponding to 8 centimeters of water between ports 38 and 40 and switch 71 is pushed closed so that exactly 4.440 volts appears at test point terminal 83. Factory adjustment of potentiometer 73 will be made under the conditions that air pressure is provided corresponding to 8 centimeters of water between ports 38 and 40 and switch 74 is pushed closed so that exactly 4.000 volts appears at the test point terminal 83.

Switch 68 is actuated for operation of the converter 32 when the flow rate of nitrous oxide, $N_2O$, will be measured. Switch 71 will be actuated for air and switch 74 for oxygen $O_2$. The corresponding push buttons will be so marked.

Note that the sensitivity of the preamplifier 100, which includes the tandem connected amplifiers 44, 64 and 66, will have three values, respectively, corresponding to closure of switches 68, 71 and 74, respectively. The ratio of the preamplifier sensitivities, for closure of switch 71 relative to that for closure of switch 74, will be 4.440/4.000 or 1.11 which is the ratio of the viscosities of oxygen to that of air. The ratio of the sensitivities of preamplifier 100, for closure of switch 68 relative to that for closure of switch 74, will be 5.520/4.000 or 1.38 which is the viscosities ratio of oxygen and nitrous oxide.

The values of resistors and potentiometers used in the circuit (FIG. 2) are provided in Table 1. Unless otherwise indicated, values are within ±10%.

TABLE 1

| Resistor | Potentiometer | Ohms |
|---|---|---|
| 42 | | 300K |
| 45 | | 762K |
| 46 | | 11K |
| 47 | | 8.2K |
| | 48 | 1K |
| 49 | | 300K |
| 50 | | 700K |
| | 51 | 100K |
| | 52 | 1K |
| 56 | | 27K |
| 57 | | 27K |
| 58 | | 2.1K* |
| 59 | | 2.1K* |
| | 60 | 500 |
| 63 | | 5K |
| 65 | | 5K |
| | 67 | 5K |
| 69 | | 5K |
| | 70 | 5K |
| 72 | | 5K |
| | 73 | 5K |
| | 82 | 10K |
| 84 | | 6K |
| | 86 | 20K |
| 96 | | 18K* |
| 97 | | 2K* |

*Values ± 1%

A preferred procedure for determining the aforementioned characterizing (sensitivity) number for a particular L.F.E. is as follows.

The pressure ports of the L.F.E. are connected via flexible tubes to the input ports 38 and 40 at the front panel 34a of converter 32. The pushbutton of switch 71 is depressed closing switches 71 and 77. This is the circuit condition for measuring the flow of air as was noted above. A standard positive displacement flow meter, e.g. Singer Model DTM-115 made by American Meter Division of Singer Corp. is connected in line with the L.F.E. With no air flowing in the L.F.E., adjust the potentiometer 48 so that volt meter 95 reads zero volts.

Assuming that the L.F.E. is a 1″ element having a nominal range of up to 100 liters/minute, establish an air flow through the L.F.E. of 80 liters/minute. The ten turn potentiometer 86 is adjusted so that the volt meter 95 reads exactly 8 (volts). Volt meter 95 is marked "10" at full scale.

Switch 79 is then closed (which opens all other switches) applying exactly 3 V to the input of driver amplifier 80, and the meter 95 is read. That meter reading is the characterizing number for that L.F.E.

Now at any time in the future when that L.F.E. will again be used, it is only necessary to connect it to the converter input ports (38 and 40), close switch 79 (applying 3 volts to driver amplifier 80), adjust the potentiometer 86 to read the characterizing number of that L.F.E. at the voltmeter, and finally depress the appropriate switch button (either of switch 68, 71 or 74) corresponding to the gas whose flow rate is to be measured.

The full scale accuracy of gas flow rate measurements made using the above procedure and a prototype converter of this invention have been better than ±1% at full scale for all three of the gasses, air, oxygen and nitrous oxide.

What is claimed is:

1. A pressure to voltage converter for use in a gas flow measuring instrument for monitoring the flow of gasses comprising a differential pressure to voltage transducer adapted for attachment to two output pressure ports of a laminar flow sensing element, and a voltage amplifier having an input connected to the output of said differential pressure to voltage transducer, said amplifier comprising a gain-steps switching means for changing the gain of said amplifier in steps from a first gain value to a second gain value wherein the ratio of said second and first gain values is equal to the ratio of the viscosities of a gas of a first kind and a gas of a second kind in anticipation that the flow rates of said gasses may be measured at one time and then another, respectively, without the need for an intervening recalibration.

2. The pressure to voltage converter of claim 1 wherein said kinds of gasses are selected from air, oxygen and nitrous oxide.

3. The pressure to voltage converter of claim 1 wherein said gain-steps switching means is additionally for changing said amplifier gain from said second gain value to a third gain value wherein the ratio of said third to said second gain values is equal to the ratio of the viscosities of a gas of said second kind to a gas of a third kind.

4. The pressure to voltage converter of claim 1 wherein said voltage amplifier is comprised of a preamplifier portion including said gain-steps switching means, a driver amplifier, a source of a DC reference voltage and a switch means for connecting the input of said driver amplifier either to the output of said preamplifier or alternately to said DC reference voltage.

5. The pressure to voltage converter of claim 4 wherein said driver amplifier includes a vernier gain adjusting means for vernierly changing the gain of said driver amplifier by which a predetermined voltage at the output of said voltage amplifier may be obtained when a gas of said first kind is flowing at a known rate through a particular laminar flow sensing element which is connected to said transducer.

6. The pressure to voltage converter of claim 1 additionally comprising a linearizing circuit means for compensating for the characteristic nonlinearity in a laminar flow element to provide at the output of said converter a voltage that is a linear function of the rate of gas flow through an attached laminar flow element.

7. The pressure to voltage converter of claim 6 wherein said linearizing circuit means is comprised of two series circuits each including a back biased diode, one end of each series circuit being connected to a point in the main electrical signal channel of said converter and the other ends of said series circuits being connected to a positive DC voltage and a negative DC voltage, respectively.

8. A pressure to voltage converter for use in a gas flow measuring instrument for monitoring the flow of gasses administered by an anesthesiologist to a patient undergoing surgery comprising:

a differential pressure to voltage transducer having two input ports adapted for attachment to two output pressure ports of a laminar flow sensing element;

a voltage amplifier having an input connected to the output of said transducer; and a housing, said transducer and said amplifier being fixedly mounted in said housing, said amplifier comprising a preamplifier connected in tandem with and followed by a driver amplifier;

said preamplifier including a gain-steps switching means for changing the gain of said preamplifier in steps from a first gain value to a second gain value whereby the ratio of said second and first gain values is equal to the ratio of the viscosities of a gas of the first kind and a gas of a second kind, the combined sensitivity of said transducer and said preamplifier operating at said first gain value having been set at a constant predetermined sensitivity as measured in output volts per centimeters of water pressure between said input ports, said driver amplifier including a vernier gain adjusting means for manually adjusting the gain of said output amplifier to obtain a predetermined voltage at the output of said voltage amplifier when said switching means is switched to said first gain value and when a gas of said first kind is flowing at a known rate through a particular laminar flow element which is connected to said transducer;

a fixed DC reference voltage source of predetermined magnitude; and a sensing-element characterization means for temporarily applying said reference voltage at the input of said output amplifier to temporarily produce a characterizing voltage at the output of said voltage amplifier to characterize said particular laminar flow element for precalibrated use in conjunction with said pressure voltage converter.

9. A plurality of pressure to voltage converters as claimed in claim 8, wherein said combined sensitivity of said transducer and preamplifier in each of said plurality of converters is the same as in each other of said converters so that said particular laminar flow sensing element having been characterized using said each converter is also properly characterized for calibrated use with any of said other converters.

* * * * *